(12) United States Patent
Oraevsky et al.

(10) Patent No.: US 7,740,585 B2
(45) Date of Patent: Jun. 22, 2010

(54) QUANTITATIVE OPTOACOUSTIC TOMOGRAPHY WITH ENHANCED CONTRAST

(75) Inventors: Alexander Oraevsky, Houston, TX (US); Sergey Ermilov, Houston, TX (US)

(73) Assignee: Seno Medical Instruments, Inc., San Antonio, TX (US)

( * ) Notice: Subject to any disclaimer, the term of this patent is extended or adjusted under 35 U.S.C. 154(b) by 542 days.

(21) Appl. No.: 11/656,103

(22) Filed: Jan. 22, 2007

(65) Prior Publication Data

US 2007/0238958 A1      Oct. 11, 2007

Related U.S. Application Data

(60) Provisional application No. 60/760,846, filed on Jan. 20, 2006.

(51) Int. Cl.
*A61B 8/00* (2006.01)
(52) U.S. Cl. ........................... 600/443; 600/407
(58) Field of Classification Search ............. 600/443
See application file for complete search history.

(56) References Cited

U.S. PATENT DOCUMENTS 5,840,023 A * 11/1998 Oraevsky et al. ............ 600/407
6,405,069 B1 * 6/2002 Oraevsky et al. ............ 600/407
2007/0015992 A1 * 1/2007 Filkins et al. ............... 600/407

OTHER PUBLICATIONS

Oraevsky, A. et al. In Vivo *Testing of Laser Optoacoustic System for Image-Guided Biopsy of Prostate: SPIE*, Mar. 6, 2006, vol. 6086, pp. 80-90.

Paltauf, G. et al. *Iterative Reconstruction Method for Three-Dimensional Optoacoustic Imaging: SPIE Proceedings of Biomedical Optoacoustics*, 2001, vol. 4256, pp. 138-146.

Spirou, G. M. et al. *Development and Testing of an Optoacoustic Imaging System for Monitoring and Guiding Prostate Cancer: Proceedings of SPIE*, 2004, vol. 5320, pp. 44-56.

* cited by examiner

*Primary Examiner*—Long V Le
*Assistant Examiner*—Hien Nguyen
(74) *Attorney, Agent, or Firm*—Benjamin Aaron Adler (57) ABSTRACT

Provided herein is an optoacoustic imaging system configured to produce images of one or more objects in a body using at least a maximum angular amplitude probability algorithm to reconstruct the optoacoustic images of the body. In addition the optoacoustic imaging system may be configured to produce 3D maps from the reconstructed optoacoustic images of the body. Also, provided is a method for diagnosing a pathophysiological condition characterized by abnormal optical properties of tissues in a body from maps so produced.

19 Claims, 5 Drawing Sheets

QUANTITATIVE OPTOACOUSTIC TOMOGRAPHY WITH ENHANCED CONTRAST

CROSS-REFERENCE TO RELATED APPLICATIONS

This application claims benefit of priority of provisional application U.S. Ser. No. 60/760,846, filed Jan. 20, 2006, now abandoned.

BACKGROUND OF THE INVENTION

1. Field of the Invention

The present invention relates to the field of optoacoustic tomography. More specifically, the present invention relates to a method of enhancing contrast during quantitative optoacoustic tomography and removing image artifacts using maximum angular amplitude probability (MAAP) reconstruction of an image.

2. Description of the Related Art

Optoacoustic tomography is used in biomedical applications for in vivo and in vitro imaging of animal and human tissues and organs based on differences in tissue optical properties. Optoacoustic tomography has the potential to become a valuable modality of functional molecular imaging. The essence of functional molecular imaging is to provide quantitative information (maps) of distributions and concentrations of various molecules of interest for medicine. For example, distribution of hemoglobin and oxi-hemoglobin concentration in tissue shows whether the tissue normally functions or it is damaged or malignant. Distribution of specific protein receptors in cell membranes give insight into molecular biology or cells helping in designing drugs and therapeutic methods to treating human diseases.

Traditionally, a radial back projection (RBP) image reconstruction algorithm is used in a laser optoacoustic imaging system (LOIS) to reconstruct two-dimensional (or three-dimensional) images of the object (such as tumor). Image blurring and the presence of artifacts in form of radiating arcs decrease resolution and clarity of the image. Most importantly, the brightness of objects or area of interest on images reconstructed with RBP is not proportional to the original amount of absorbed optical energy. This occurs due to the fact that each receiving transducer with wide angular aperture can integrate information received from a number of objects in the volume being imaged, so that the brightness of any specific object is altered upon radial back projection of signal amplitudes integrated over the spherical surface within the field of view of each transducer.

Thus, a recognized need is present in the art for improved quantitative optoacoustic tomography procedures. Specifically, the prior art is deficient in methods applying algorithms effective to significantly improve the (1) accuracy of quantitative information displayed on optoacoustic images and (2) contrast of optoacoustic images (relative contribution of image artifacts). More specifically, the prior art is deficient in using maximum angular amplitude probability reconstruction algorithm to provide for clear visualization of real optical absorbers and improved estimation of absorption coefficients of specified discrete absorbers. The present invention fulfils this longstanding need in the art.

SUMMARY OF THE INVENTION

The present invention is directed to an optoacoustic imaging system for producing images of one or more objects in a body. The optoacoustic imaging system is configured to perform the steps of illuminating a body using pulses of electromagnetic radiation and generating distribution of absorbed thermal energy under illumination conditions of temporal pressure confinement within a volume of a resolution of interest, detecting temporarily resolved profiles of optoacoustic signals resulting therefrom, processing signals to determine a value of absorbed electromagnetic energy, and reconstructing high-contrast optoacoustic images of the body from determined optical absorption coefficients of one or more objects therewithin using at least a maximum angular amplitude probability algorithm. The present invention is directed to a related optoacoustic imaging system configured to perform the further step of plotting a map of the one or more objects using the determined optical absorption coefficients.

The present invention also is directed to an optoacoustic imaging system for producing maps of one or more objects in a body. The optoacoustic imaging system is configured to perform the steps of illuminating the body with pulses of electromagnetic radiation thereby producing a homogeneous distribution of an energy fluence within any given plane inside the body perpendicular to the direction of the incident beam of the electromagnetic radiation and detecting temporarily resolved profiles of resulting optoacoustic signals using an array of ultrawide-band ultrasonic transducers with transducer directivity of about 0 to about $2\pi$ steradians and with an angular aperture of the array of about 0 and $4\pi$ steradians. The temporarily resolved signals are amplified and digitally recorded using an electronic data acquisition system with subsequent filtering out all digitally recorded signals from noise while keeping the profiles of the optoacoustic signals unaltered. The the temporalily resolved signals are optimally processed to convert bipolar pressure signals into monopolar signals with amplitude proportional to the absorbed thermal energy. Optoacoustic images of the body are reconstructed using a radial backprojection algorithm to determine a probability for each sample of an optoacoustic signal to be received from a particular direction relative to the transducer and applying a maximum angular amplitude probability algorithm effective to use information on the direction of the received optoacoustic signals relative to the transducer thereby reconstructing high-contrast optoacoustic images of the body showing location and shape of the object(s). Each reconstructed arc is fitted with a polynomial function, the second derivative is calculated to determine exact boundaries of the objects and each of the determined objects inside the body is assigned with an unknown absorption coefficient. Each sample of the integral of the temporarily resolved optoacoustic profiles received by each transducer is used to solve a linear regression model of unknown absorbtion coefficients with regression coefficients related to determined sizes of the objects. The optoacoustic map is then plotted based on determined absorption coefficients of the objects inside the body.

The present invention is directed further to a method for diagnosing a pathophysiological condition characterized by abnormal optical properties of tissues in a body. The method comprises obtaining temporarily resolved profiles of acoustic signals generated by one or more objects associated with the pathophysiological condition within a body upon illumination thereof with electromagnetic radiation, applying at least a maximum angular amplitude probability algorithm to the profiles to determine optical absorption coefficients of the one or more objects to reconstruct high-contrast optoacoustic images of the body; and plotting an optoacoustic map based on the determined optical absorption coefficient(s) of the object(s) showing a location thereof inside the body thereby diagnosing the pathophysiological condition.

Other and further aspects, features, benefits, and advantages of the present invention will be apparent from the following description of the presently preferred embodiments of the invention given for the purpose of disclosure.

BRIEF DESCRIPTION OF THE DRAWINGS

The appended drawings have been included herein so that the above-recited features, advantages and objects of the invention will become clear and can be understood in detail. These drawings form a part of the specification. It is to be noted, however, that the appended drawings illustrate preferred embodiments of the invention and should not be considered to limit the scope of the invention.

FIGS. 1A-1B depict the optoacoustic imaging system used to acquire images presented in FIGS. 2A-2D and 3A-3D. This system employs orthogonal illumination relative to the array of ultrawide-band ultrasonic detectors.

DETAILED DESCRIPTION OF THE INVENTION

In one embodiment of the present invention there is provided an optoacoustic imaging system for producing images of one or more objects in a body, configured to perform the steps of a) illuminating a body using pulses of electromagnetic radiation; b) generating distribution of absorbed thermal energy under illumination conditions of temporal pressure confinement within a volume of a resolution of interest; c) detecting temporarily resolved profiles of optoacoustic pressure signals resulting therefrom; d) processing signals to determine a value of absorbed electromagnetic energy; and e) reconstructing high-contrast quantitative optoacoustic images of the body from determined optical absorption coefficients of one or more objects therewithin using at least a maximum angular amplitude probability algorithm.

Further to this embodiment the optoacoustic imaging system may be configured to perform the step of plotting a map of the one or more objects using the determined optical absorption coefficients. In this further embodiment the map of the one or more objects comprises a tool for a diagnosis of a pathophysiological condition of the body characterized by abnormal tissue morphology or to establish the location and the absolute value of the same. Examples of the pathophysiological condition are a breast cancer, a prostate cancer, skin cancer, a vascular skin disorder, a brain hemorrhage, a hematoma, a heart disease, atherosclerotic plaques, arthritis, an ocular disease, any tissue deprived from blood supply due to the pathophysiological condition or other condition with abnormal optical properties of tissues.

In these embodiments the illuminating step may comprise delivering pulses of electromagnetic radiation to the body thereby producing a homogeneous distribution of an energy fluence within any given plane inside the body that is perpendicular to the direction of the incident beam of the electromagnetic radiation. Also, in these embodiments the detecting step may comprise a) receiving the optoacoustic signals through an array of ultrawide-band ultrasonic transducers; or b) receiving the optoacoustic signals with a single ultrawide-band ultrasonic transducer scanned along the body.

In addition, in these embodiments the processing step may comprise a) amplifying and digitally recording the temporarily resolved signals using an electronic data acquisition system; b) filtering all digitally recorded signals from noise while keeping the profiles of the optoacoustic signals unaltered; c) calculating either an integral of the temporally resolved optoacoustic signals or their time-derivative or a combination thereof resulting in enhanced contrast and optimal signal processing for quantitative analysis; and d) determining signal amplitude generated by objects only on those ultrasonic transducers that could separate all objects of diagnostic interest by detecting them at different time positions. The transducers may have a transducer directivity of about 0 to about $2\pi$ steradians with an angular aperture of the array of about 0 and $4\pi$ steradians.

Furthermore, in these embodiments the reconstructing step may comprise a) determining a probability for each sample of the acoustic signal to be received from a particular direction relative to the transducer using a radial backprojection algorithm; b) applying a maximum angular amplitude probability algorithm effective to use information on the direction of the received acoustic signals relative to the transducer receiving the signal thereby reconstructing the high-contrast optoacoustic images of the body showing location, shape and true brightness of the one or more objects; c) fitting each reconstructed arc with a polynomial function and calculating the second derivative to determine exact boundaries of the object (s); d) assigning each of the determined objects inside the body with an unknown absorption coefficient; and e) using each sample of the integral of the temporarily resolved optoacoustic profiles received by each transducer to solve a linear regression model of unknown absorbtion coefficients with regression coefficients related to determined sizes of the one or more objects.

In an alternate aspect the object may be a single object and step e) comprises a) using each sample of the integral of the temporarily resolved optoacoustic profiles received by each transducer to calculate an average absorption coefficient of an arc in the object while accounting for individual size of the image pixel and the number of pixels in the arc within the object; and b) using statistical distribution of the average absorption coefficients of the arcs to estimate the true absorption coefficient of the object. In another alternate aspect the directivity of each transducer may be about zero and step e) comprises placing measured sample values of the integrated optoacoustic signals to the pixels of the map along the line of directivity of each acoustic transducer.

In another embodiment of the present invention there is provided an optoacoustic imaging system for producing maps of one or more objects in a body, configured to perform the steps of a) illuminating the body with pulses of electromagnetic radiation thereby producing a homogeneous distribution of an energy fluence within any given plane inside the body perpendicular to the direction of the incident beam of the electromagnetic radiation; b) detecting temporarily resolved profiles of resulting optoacoustic signals using an array of ultrawide-band ultrasonic transducers with transducer directivity of about 0 to about $2\pi$ steradians and with an angular aperture of the array of about 0 and $4\pi$ steradians; c) amplifying and digitally recording the temporarily resolved signals using electronic data acquisition system; d) filtering all digitally recorded signals from noise while keeping the profiles of the optoacoustic signals unaltered; e) optimally processing the temporalily resolved signals to convert bipolar pressure signals into monopolar signals with amplitude proportional to the absorbed thermal energy; f) reconstructing optoacoustic images of the body using a radial backprojection algorithm effective to determine a probability for each sample of an optoacoustic signal to be received from a particular direction relative to the transducer; g) applying a maximum angular amplitude probability algorithm effective to apply information on the direction of the received optoacoustic signals relative to the transducer thereby reconstructing high-contrast optoacoustic images of the body showing location and shape of the one or more objects; h) fitting each reconstructed arc with a polynomial function and calculating the second derivative to determine exact boundaries of the object(s); i) assigning each of the determined objects inside the body with an unknown absorption coefficient; j) using each sample of the integral of the temporarily resolved optoacoustic profiles received by each transducer to solve a linear regression model of unknown absorbtion coefficients with regression coefficients related to determined sizes of the objects; and k) plotting the optoacoustic map based on determined absorption coefficients of the one or more objects inside the body.

In a related embodiment, the object may a single object and step i) comprises a) using each sample of the integral of the temporarily resolved optoacoustic profiles received by each transducer to calculate an average absorption coefficient of an arc in the object while accounting for individual size of the image pixel and the number of pixels in the arc within the object; and b) using statistical distribution of the average absorption coefficients of the arcs to estimate the true absorption coefficient of the object.

In another related embodiments the directivity of each transducer may be about zero and step i) comprises reconstructing the optoacoustic images of the body by placing measured sample values of the integrated optoacoustic signals to the pixels of the map along the line of directivity of each acoustic transducer.

In all embodiments the map of the one or more objects may comprise a tool for diagnosis of a pathophysiological condition of the body characterized by abnormal tissue morphology or to establish the location and absolute value of the same. Examples of the pathophysiological condition are a breast cancer, a prostate cancer, skin cancer, a vascular skin disorder, a brain hemorrhage, a hematoma, a heart disease, atherosclerotic plaques, arthritis, an ocular disease, any tissue deprived from blood supply due to the pathophysiological condition or other condition with abnormal optical properties of tissues In yet another embodiment of the present invention there is provided a method for diagnosing a pathophysiological condition characterized by abnormal optical properties of tissues in a body, comprising a) obtaining temporarily resolved profiles of acoustic signals generated by one or more objects associated with the pathophysiological condition within a body upon illumination thereof with electromagnetic radiation; b) applying at least a maximum angular amplitude probability algorithm to the profiles to determine optical absorption coefficients of the one or more objects to reconstruct high-contrast optoacoustic images of the body; and c) plotting an optoacoustic map based on the determined optical absorption coefficient(s) of the object(s) showing a location thereof inside the body thereby diagnosing the pathophysiological condition. Further to this embodiment, the method may comprise administering an optoacoustic contrast agent effective to alter optical absorption of specific objects or locations of diagnostic interest in the body.

In these embodiments the electromagnetic radiation may be pulsed thereby producing a homogeneous distribution of an energy fluence within any given plane inside the body that is perpendicular to the direction of the incident beam of the electromagnetic radiation. Also in these embodiments the obtaining step may comprise a) receiving the acoustic signals through an array of ultrawide-band ultrasonic transducers; b) amplifying and digitally recording the temporarily resolved signals using an electronic data acquisition system; and c) filtering all digitally recorded signals from noise while keeping the profiles of the acoustic signals unaltered. The transducers may be as described supra.

Also in these embodiments the applying step may comprise a) determining a probability for each sample of the acoustic signal to be received from a particular direction relative to the transducer using a radial backprojection algorithm; b) applying a maximum angular amplitude probability algorithm effective to use information on the direction of the received acoustic signals relative to the transducer receiving the signal thereby reconstructing the high-contrast optoacoustic images of the body showing location and shape of one or more objects; c) fitting each reconstructed arc with a polynomial function and calculating the second derivative to determine exact boundaries of the object(s); d) assigning each of the determined objects inside the body with an unknown absorption coefficient; and e) using each sample of the integral of the temporarily resolved optoacoustic profiles received by each transducer to solve a linear regression model of unknown absorbtion coefficients with regression coefficients related to determined sizes of the objects. In alternate aspects the object may be a single object and the transducer directivity may be about zero as described supra. In all embodiments the pathophysiological condition may be as described supra.

As used herein, the term "a" or "an" when used in conjunction with the term "comprising" in the claims and/or the specification may mean "one," but it is also consistent with the meaning of "one or more," "at least one," and "one or more than one." As used herein, the term "or" in the claims is used to mean "and/or" unless explicitly indicated to refer to alternatives only or the alternatives are mutually exclusive, although the disclosure supports a definition that refers to only alternatives and "and/or."

As used herein, the phrase "pathophysiological condition" refers to any deleterious conditions involving abnormal optical properties of tissues, such as cancer, diseases and disorders related to inflammation, tissues with abnormal blood supply, blood vessels, atherosclerotic plaque, heart, skin diseases and disorders, ocular diseases and disorders, conditions resulting from hemorrhage, hematomas, arthritis, etc. As is well known in the art, a tumor may be malignant, such as a cancer, or non-malignant and characterized by a benign tumor or other abnormal tissue growth.

As used herein, the term "body" refers to a recipient of optoacoustic imaging, preferably a mammal, more preferably a human.

The present invention provides an image reconstruction algorithm, maximum angular amplitude probability (MAAP), that significantly improves the contrast of optoacoustic images, removes ghost images, arc artifacts, and allows clear visualization quantitative measurement of maps of absorbers of electromagnetic energy. More importantly it can be used for post-processing estimation of absorption coefficients for specified discrete absorbers. These two improvements put an optoacoustic tomography system on a new level, making it a powerful tool for visualization and diagnostics of pathological conditions manifesting in a changed absorption coefficient, in, for example, but not limited to, tumors associated with a cancer. Thus, it is contemplated that the system of quantitative optoacoustic tomography or imaging and the algorithms provided herein are useful to improve diagnosis of a pathophysiological condition.

Particularly, provided herein is an optoacoustic imaging system (FIGS. 1A-1B) for producing 2D, and, by extension, 3D images of one or more objects in a body. The system utilizes a hemicylindrical transducer array of ultrawide-band ultrasound transducers with an illumination system orthogonal to the plane of optoacoustic image. The transducer array is effective for quantitative imaging to measure the axial depth distribution of the optical illumination at a site of interest, for example, but not limited to, a breast, in the body.

Figure 1A:
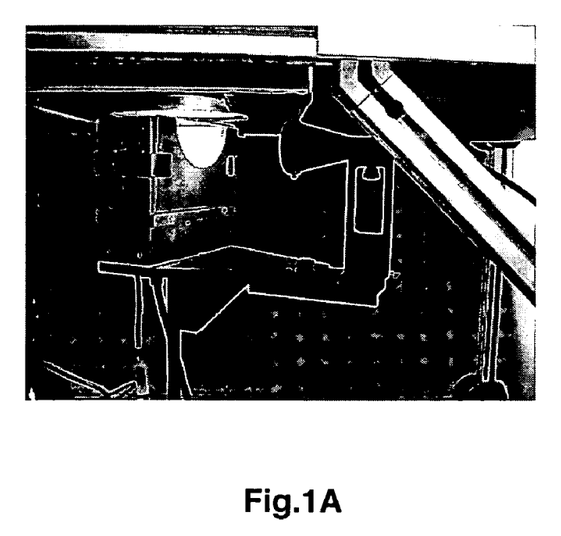
FIG. 1A shows the hemicylindrical transducer array with the illumination system orthogonal to the plane of optoacoustic image.
Figure 1B:
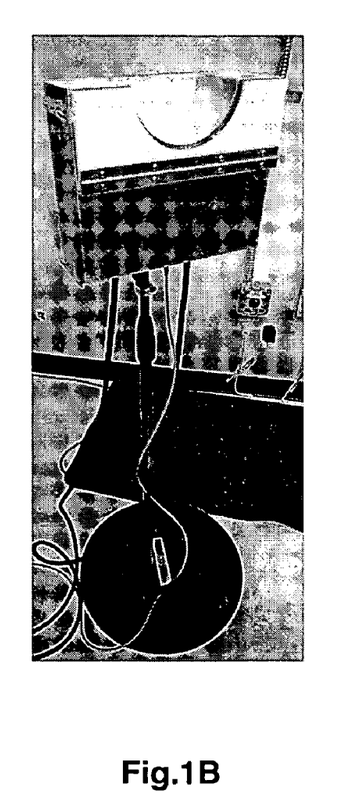
FIG. 1B shows the breast imaging probe with hemicylindrical array of ultrawide-band ultrasound transducers for quantitative imaging and 2D array which are located on the back (not shown) for measurement of axial depth distribution of optical illumination in the breast.

The optoacoustic imaging system may be configured to perform a series of steps to obtain the image. The body is illuminated using electromagnetic radiation (EMR). Temporarily resolved profiles of optoacoustic signals resulting from thermal expansion of an EMR heated body with heterogeneous distribution of absorbing structures are detected. High-contrast optoacoustic images of the body are reconstructed from determined optical radiation absorption coefficients of one or more objects therewithin using at least a maximum angular amplitude probability algorithm as shown in the Examples below. In addition, the optoacoustic imaging system may be configured to plot a map of the one or more imaged objects thereby accurately reproducing the shape of these objects and their original brightness using the determined optical absorption coefficients.

Preferably, the optoacoustic imaging system may be configured to illuminate the body with pulses of electromagnetic radiation thereby producing a homogeneous distribution of an energy fluence within any given plane inside the body perpendicular to the direction of the incident beam of the electromagnetic radiation. The temporarily resolved profiles of resulting optoacoustic signals may be detected using an array of ultrawide-band ultrasonic transducers with a transducer directivity of about 0 to about $2\pi$ steradians and with an angular aperture of the array of about 0 and $4\pi$ steradians. The temporarily resolved signals are amplified and digitally recorded using an electronic data acquisition system with subsequent filtering out of noise while keeping the profiles of the optoacoustic signals unaltered.

The optoacoustic images of the body may be reconstructed using a radial backprojection algorithm to determine a probability for each sample of an optoacoustic signal to be received from a particular direction relative to the transducer and, subsequently, applying a maximum angular amplitude probability algorithm effective to use information on the direction of the received optoacoustic signals relative to the transducer. The reconstructed high-contrast optoacoustic images of the body show location, shape and true absorbed energy (brightness) of the object(s). Each reconstructed arc, in the case of 2D imaging, or spherical surface, in the case of 3D, is fitted with a polynomial function, the second derivative is calculated to determine exact boundaries of the objects and each of the determined objects inside the body is assigned with an unknown absorption coefficient proportional to the thermal energy absorbed in the objects. The capability of the disclosed imaging system to display distribution of the absorption coefficient for electromagnetc radiation can be enabled by two factors: (1) design of electromagnetic illumination resulting in homogeneous distribution of energy fluence within at least one image plane (slice) and (2) use of MAAP algorithm for correction of the optoacoustic image reconstructed using RBP.

Thus, the optoacoustic imaging systems provided herein are useful for diagnosing a pathological or physiological condition characterized by abnormal optical properties of certain volumes of tissues, such as, but not limited to, tumors associated with neoplastic diseases, blood vessels, the heart, hematomas or other tissues containing oxygenated and deoxygenated hemoglobin. More specifically, without being limiting, the pathophysiological condition may be a breast cancer, a prostate cancer, a skin cancer, a vascular skin disorder, a brain hemorrhage, a hematoma, a heart disease, atherosclerotic plaques, arthritis, an ocular disease, or any tissue deprived from blood supply due to the pathological or physiological condition.

The diagnostic methods provided herein may comprise obtaining temporarily resolved profiles of acoustic signals generated by one or more objects associated with the pathophysiological condition within the body upon illumination thereof with electromagnetic radiation. At least the maximum angular amplitude probability algorithm is applied to the profiles to determine optical absorption coefficients of the one or more objects to reconstruct high-contrast optoacoustic images of the body. Thus, an optoacoustic map may be plotted based on the determined optical absorption coefficient(s) of the object(s) showing a location thereof inside the body thereby diagnosing the pathophysiological condition.

Furthermore, the method may comprise administering an optoacoustic contrast agent prior to imaging and mapping the optical absorption coefficient(s) of the objects. These contrast agents are effective to alter the optical absorption of specific objects or locations of diagnostic interest in the body. Effective optoacoustic contrast agents are well-known and standard in the art.

It is well known to those skilled in the art of optoacoustic imaging that acoustic waves propagate as expanding spheres in three-dimensions. Thus, it is possible to reconstruct 3D optoacoustic maps by placing ultrasonic transducers in appropriate locations in 3D space or scanning at least one ultrasonic transducer to collect optoacoustic signals from the 3D space. The present invention also encompasses an optoacoustic imaging system for producing 3D maps of one or more objects in a body. Some examples and preferred embodiments given in this invention describe two-dimensional imaging system, two dimensional images and other two-dimensional considerations. These systems, images and considerations, may be without limitations applied to a three-dimensional optoacoustic tomography. One skilled in the art can understand that a circle on a 2D image corresponds to a sphere on 3D image and an arc in 2D space corresponds to a spherical surface segment in 3D space. All other similar consideration can be without limitations transferred from the 2D space to the 3D space.

Temporarily resolved optoacoustic profiles received by each transducer are used to solve a linear regression model of unknown absorption coefficients with regression coefficients related to determined sizes (shapes) of the objects. The measured optoacoustic value proportional to the absorption coefficient can be calculated either based on the time integral of the optoacoustic profile or on the time derivative of the optoacoustic profile. As an example, let us take a spherical object evenly heated with electromagnetic energy, so that an N-shaped bipolar acoustic pressure wave profile is generated. In optoacoustic tomography, one is interested in mapping absorbed energy, a monopolar value, which can be calculated based on bipolar detected pressure signals. Thus, one can use either a time integral or time-derivative of the optoacoustic pressure signal to map the absorbed energy. The integral and the derivative of the optoacoustic N-wave signal between the boundaries of the objects are both proportional to the absorbed electromagnetic energy (and, in case of homogeneous light distribution, to the absorption coefficient). However, each way of signal processing has its own limitations. The integral may result in reduced sharpness of the boundaries (bell function approximation of a rectangle), while the derivative may result in reduced object contrast between very bright sharp boundaries. One optimal solution is to employ a combination of integrated and differentiated signals. When a true value absorbed energy is determined from the raw optoacoustic signals, the optoacoustic map is then plotted based on determined absorption coefficients of the objects inside the body.

As one possible designs of the system, which produces homogeneous distribution of energy fluence at least in one plane or multiple plane parallel to each other, this invention teaches illumination of the body with pulses of electromagnetic radiation directed orthogonally to the ultrawide-band ultrasonic detection. One or more ultrawide-band ultrasonic transducers can, in this design, detect optoacoustic signals with amplitude proportional to the absorption coefficient. One skilled in the art can anticipate a number of potential system designs in which the distribution of electromagnetic energy fluence will be homogeneous at least for one slice (plane). Also, hardware and software compensation can be applied to transform relatively heterogeneous distribution of electromagnetic energy (such as near-infrared light) into relatively homogeneous distribution.

Theoretical Concepts of OA Tomography

The equation governing distribution of the acoustic velocity potential ($\Phi$) inside a medium, homogeneously illuminated with a short laser pulse is:

$$\left(\nabla^2 - \frac{1}{c_s^2}\frac{\partial^2}{\partial t^2}\right) f? = \frac{\beta}{\rho \cdot C_p} \mu_a(\bar{r}) E_0 \delta(t) \quad \text{(eq. 1)}$$

where $c_s$ is speed of sound inside the medium; t is time beginning from the moment of laser energy deposition; $\beta$ is the isobaric volume expansion coefficient; $\rho$ is the medium density; $C_p$ is the specific heat capacity at constant pressure; $\mu_a$ is the medium absorption coefficient; $E_0$ is the energy fluence; and $\delta$ is the delta function. The inverse problem of optoacoustic tomography is to calculate distribution of $\mu_a(\bar{r})$, knowing temporal profiles of the acoustic velocity potential at a finite number of spatial locations $f?(\bar{r}_{Tk}, t)$, k=1 ... NT.

The problem embodied in equation (1) can be solved in a discrete (m×n×p) Cartesian coordinate system as a superposition of m×n×p single-source problems:

$$\left(\nabla^2 - \frac{1}{c_s^2}\frac{\partial^2}{\partial t^2}\right) f?_{ijk}(\bar{r}, t) = \frac{\beta}{\rho \cdot C_p} \mu_{aijk} E_0 \delta(t) \quad \text{(eq. 2)}$$

where i=1 ... m; j=1 ... n; k=1 ... p; and $\mu_{aijk}$ is a single absorptive spherical element (pixel) having radius $R_p$ and a center spatially located at $r_{ijk}$. The radius $R_p$ can be determined from the isometric condition:

$$V_p = \frac{4}{3}\pi R_p^3 = \Delta R^3 \text{ or } R_p = \Delta R \sqrt[3]{\frac{3}{4\pi}} \quad \text{(eq. 3)}$$

where $\Delta R$ is the length of a cubic pixel.

For $C_s$, $\rho$, $\beta$, and $C_p$ independent of $\bar{r}$ and t, equation (2) has an exact solution in equation (4) below:

$$\begin{cases} f?_{ijk}(\bar{r}, t) = \frac{K_{ijk}}{2|\bar{r} - \bar{r}_{ijk}|}\left(0.5t^2 - \frac{|\bar{r} - \bar{r}_{ijk}|}{c_s}t + f?_{0ijk}\right), \\ \qquad t \in \left[\frac{|\bar{r} - \bar{r}_{ijk}| - R_p}{c_s}; \frac{|\bar{r} - \bar{r}_{ijk}| + R_p}{c_s}\right] \\ f?_{ijk}(\bar{r}, t) = 0, t \notin \left[\frac{|\bar{r} - \bar{r}_{ijk}| - R_p}{c_s}; \frac{|\bar{r} - \bar{r}_{ijk}| + R_p}{c_s}\right] \end{cases} \quad \text{(eq. 4)}$$

where $$K_{ijk} = \frac{\mu_{aijk}\beta E_0 c_s^3}{\rho C_p},$$

and $\Phi_{0ijk}$ can be found from the continuity condition:

$$f?_{ijk}\left(\bar{r}, \frac{|\bar{r} - \bar{r}_{ijk}| - R_p}{c_s}\right) = f?_{ijk}\left(\bar{r}, \frac{|\bar{r} - \bar{r}_{ijk}| + R_p}{c_s}\right) = 0 \quad \text{(eq. 5)}$$

resulting in $$f?_{0ijk} = \frac{|\bar{r} - \bar{r}_{ijk}|^2 - R_p^2}{2c_s^2}.$$

One skilled in the art can envision a number of methods for deduction of absorbed energy from the measured optoacoustic signals. One possibility to measure a value linearly proportional to the absorbed energy in the body is to determine velocity potential from the measured optoacoustiv signals. Velocity potential is measured by a transducer and is averaged over the sampling period. Therefore, if the sampling period is equal to the time required for sound to travel one pixel, than the measured velocity potential is:

$$\overline{f?}_{ijk}(\vec{r}) = -\frac{K_{ijk} R_p^2}{6c_s^2 |\vec{r} - \vec{r}_{ijk}|} \quad \text{(eq. 6)}$$

Total acoustic velocity potential measured by a transducer at a sample time $t_s$ will result as a sum of average velocity potentials generated by individual pixels (eq.6), which are located on a sphere with the transducer in origin and radius equal to $c_s t_s$.

$$f?_{tr}(t_s) = -\frac{R_p^2}{6c_s^3 t_s} \sum_{S_{ts}} K_{ijk} \quad \text{(eq. 7)}$$

Equation (7) shows that at each particular time moment, $t_s$, the measured acoustic velocity potential is proportional to the linear composition of absorption coefficients measured over the sphere with a center at $\vec{r}_{tr}$ and a radius of $c_s t_s$.

It is contemplated that instead of $\Phi_{tr}$, $U_{tr} = -\rho \Phi_{tr}$ is considered, which can be calculated as temporal integral of the pressure signal. Also, to simplify the analysis, a new parameter related to the absorption coefficients is introduced:

$$K_{ijk} = \frac{\rho K_{ijk} R_p^2}{6c_s^3} = \frac{\mu_{aijk} \beta E_0 R_p^2}{6 C_p} \quad \text{(eq. 8)}$$

which transforms Eq. 7 to:

$$U_{tr}(t_s) = \frac{1}{t_s} \sum_{S_{ts}} K_{ijk}. \quad \text{(eq. 9)}$$

Directivity of a transducer, a concept introduced for any finite-sized ultrasonic transducer, plays an important role in optoacoustic image reconstruction. The voltage signal generated by a planar acoustic transducer sensing a spherical acoustic wave emitted by a pressure source located in the far field of the transducer:

$$V_{tr}(r, \theta, t) = P_0(t) * H(\theta, t) \cdot (k_n \cos\theta + k_\tau \sin\theta) \frac{r_0}{r} \quad \text{(eq. 10)}$$

where $P_0(t)$ is the pressure signal at the source surface, * indicates temporal convolution, and $H(\theta, t)$ is the directivity emission-detection function:

$$H(\theta, t) = \frac{1}{a(\theta)} \Pi\left(\frac{t}{a(\theta)}\right) \quad \text{(eq. 11)}$$

$$a(\theta) = \frac{L \sin\theta}{c_s} \quad \text{(eq. 12)}$$

where $\Pi$ is the rectangle function, L is the width of the acoustic transducer, $c_s$ is the speed of sound, $k_n$ and $k_\tau$ are the respective normal and shear acoustic sensitivity of the transducer, and $r_0$ is the initial radius of the acoustic wave front emitted by the source.

From equation (11): $H(0,t) = \delta(t)$, and therefore:

$$V_{tr}(r, 0, t) = P_0(t) k_n \frac{r_0}{r} \quad \text{(eq. 13)}$$

i.e. the signal received at the right angle to the transducer surface is not distorted by the angular sensitivity, which is intuitive. For the case of an arbitrary incident angle $\theta$, equation (10) can be reshaped into a computationally-convenient form:

$$V_{tr}(r, \theta, t) = \frac{c_s}{L} (k_n \ctg\theta + k_{\hat{\partial}}) \frac{r_0}{r} \int_{t-0.5a(\theta)}^{t+0.5a(\theta)} P_0(t) dt \quad \text{(eq. 14)}$$

Furthermore, it is assumed that the acoustic transducer is sensitive only to the normal stress component, i.e. $k_\tau = 0$, leading to:

$$V_{tr}(r, \theta, t) = \frac{c_s}{L} \ctg\theta \int_{t-0.5a(\theta)}^{t+0.5a(\theta)} V_{tr}(r, 0, t) dt \quad \text{(eq. 15)}$$

Equation (15) shows that a signal received by a planar transducer at a certain angle $\theta$ to the normal of its surface will be averaged over the temporal interval $a(\theta)$, and weighed by the factor $\cos\theta$.

Radial Back Projection (RBP) Image Reconstruction Algorithm

Radial back projection image reconstruction algorithm is traditionally used in laser optoacoustic imaging system (LOIS) to obtain 2-D images from integrated pressure signals measured by optical acoustic (OA) transducers. It employs the relationship (9) considering equal $K_{ijk}$ for elements of a particular sphere ($K_{sph}[t,s]$), formed using the sample s of the transducer t. In this case $K_{sph}[t,s]$ is proportional to the integrated optical acoustic signal and for a thin absorptive slice or narrow out-of-plane transducer sensitivity:

$$K_{sph}[t, s] \approx \frac{R_p U_{tr}[t, s]}{c_s \alpha[t, s]} \quad \text{(eq. 16)}$$

where $\alpha[t,s]$ is a piece-wise total planar angle of absorptive part of a slice or $2\pi$ if the whole slice is absorptive Then each pixel of the radial back projection-reconstructed image has a magnitude of:

$$M_{RBP}[i, j] = c_s \sum_t K_{sph}[t, s]_j \quad \text{(eq. 17)}$$

where $K_{sph}[t,s]_j$ identifies the arc introduced by a t-th transducer and passing through pixel [i,j]. Analysis of equation (17) shows that the magnitude of each pixel reconstructed using radial back projection algorithm incorporates three terms. The first term in the equation is proportional to the parameter of interest $K_{ijk}$ with position-dependent coefficients. The second and third terms are position-dependent and position-independent backgrounds, respectively. This complex structure of a reconstructed radial back projection image makes it inappropriate for quantitative optical acoustic tomography. Additionally, the image contrast is highly-dependent upon the spatial distribution of the absorptive areas. Significant arc-shaped artifacts are known to appear from highly-absorptive objects, which eventually distort images of other low-absorptive objects and even can introduce "ghost" images created by intersection of several arc-shaped artifacts.

Maximum Angular Amplitude Probability (MAAP) Approach to High-Contrast, High-Resolution Optoacoustic Tomography Quality of the optical acoustic image reconstructed using the radial back projection algorithm can be significantly improved where the background is removed and only "true" absorptive objects are displayed if equation (9) takes into account different $K_{ijk}$ along the sphere $S_{ts}$. It is impossible to get this information directly unless transducers have very narrow 3-D directivity patterns, which, practically, is very difficult to implement. However, careful analysis of a radial back projection image shows that it may be used to determine part(s) of each constitutive arc, which has a maximum probability to generate a particular sample of a signal measured by the transducer. Therefore, a radial back projection image represents a probability map for each constitutive arc. The region of maximum radial back projection intensity along the arc corresponds to the region, which has maximum probability of generating a particular signal sample, and only that area has to be used in reconstruction of the refined image.

It is demonstrated herein that the maximum angular amplitude probability reconstruction using a single maximum along each particular arc, although giving the most accurate locations of the true optical acoustic sources, creates very inhomogeneous granular images even from very homogeneous simple-shaped objects, which are difficult to interpret. A more sophisticated algorithm includes detection of an arc maximum and all the pixels around it contributing to that maximum, which, for example, may be done in the following two steps. First, all the pixels around the arc maximum with continuously reducing radial back projection magnitude are retained. Second, a third-order polynomial is used to interpolate the retained pixels versus radial back projection magnitude and only pixels which contribute to the convex part of the interpolation are used in the final image reconstruction. This procedure accurately defines the boundaries of the object of diagnostic interest in the body. Other methods for retaining all pixels contributing to the maximum value of the arc can be employed. This approach saves homogeneity of the image, while removing the tails of the arcs, which contribution to the measured optical acoustic signal is insignificant. Generally, maximum angular amplitude probability algorithm removes excessive background, ghost images, and arc artifacts, which, while due to the large number of samples and differently oriented transducers, still reconstructs every true absorptive object.

Quantitative Assessment of Absorption Coefficients for Quantitative OA Tomography The theoretical basis described herein is used, as an example, for quantitative estimation of the absorption coefficients. It should be recognized, however, that the method disclosed here for quantitative measurement of the absorption coefficient, should not be construed as the only possible method. Since, certain optoacoustic signals disclosed in this invention contain amplitude values proportional to the absorption coefficient, various accurate methods of mathematical processing can be applied to determine the absorption coefficient and then plot the determined values into objects accurately defined by the disclosed MAAP algorithm.

Equation (9) describes the most general case, where each pixel is represented by a specific absorption coefficient, and results in a very large number of linear equations relating the measured integrated optical acoustic signals to the absorption of the specimen. In clinical cancer diagnostics, the problem described by equation (9) is adequately represented by a finite number of fairly large absorbers, containing at least several pixels, surrounded by a homogeneous medium or background. The size of the background results in the low-frequency optical acoustic signals, which can be effectively filtered by electronics, and, therefore, the measured optical acoustic signals will contain only the information about the objects of interest.

If the location and boundary of absorptive objects are accurately known, than the number of unknown absorption coefficients in the system of equations (9) can be reduced from the total number of pixels to the number of objects of interest. This reduction of unknown parameters leads to the multiple linear regression model, which considering very large number of measured values of optical acoustic signals, results in accurate estimation of the average absorption coefficients of the objects of interest. The summation (eq. 9) over the entire sphere can then be split into several summations over the sphere intersections with the objects of interest.

The importance of accurate estimation of the objects location and the boundary cannot be overestimated, which as demonstrated herein can be achieved by implementing the maximum angular amplitude probability image reconstruction algorithm. MAAP images easily allow finding the number of pixels (3) from each object of interest, which contribute to a particular signal sample. Then Eq. (9) will transform to:

$$U_{tr}(t_s) = \frac{1}{t_s} \sum_{i=1}^{N_{obj}} N_{i,tr,s} K_i \qquad \text{(eq. 18)}$$

where $N_{obj}$ is a total number of objects of interest; $N_{i,tr,s}$ is number of pixels resulting from the intersection of the i-th object and a sphere with center at tr-th transducer and radius defined by the s-th sample; and $K_i$ is a parameter (eq. 8) related to the absorption coefficient of the i-th object. $N_{i,tr,s}$ is found using maximum angular amplitude probability images and multiple linear regression with a constraint on the zero free coefficient is performed to find $K_i$. The final step of the quantitative optoacoustic tomography is to fill the boundaries of the object of diagnostic interest accurately reconstructed by MAAP with absolute values of the absorption coefficients determined from the analysis of the optoacoustic signal profiles.

The following examples are given for the purpose of illustrating various embodiments of the invention and are not meant to limit the present invention in any fashion.

EXAMPLE 1

Image Reconstruction Algorithm Based on MAAP

A detailed maximum angular amplitude probability algorithm described as it is implemented in the LOIS is provided in this example.

Data Inherited from the Current Image Reconstruction:

$U_i$—integrated signal from i-th transducer (i=1 ... $N_{tr}$);

I—m×n matrix (old image) reconstructed using radial back-projection;

MAAP Image Reconstruction:

1. Create an m×n matrix I' of ZEROS.

2. For each temporal sample j (j=1 ... $N_s$) of a signal $U_i$ find corresponding elements of the matrix I (physical positions (on a real probe) of those matrix I elements should have the same distance to i-th transducer equal to $c_s(j-1)\Delta t$; where $c_s$–speed of sound, and $\Delta t$ is the temporal resolution of a transducer).

3. Find the maximum of those elements and all elements around maximum, which satisfy the relationship:

$$\{I_{max}\} : \begin{cases} I(k) > I(k+2), k > k_{max} \\ I(k) > I(k-2), k < k_{max} \end{cases} k = 1 \ldots ARC[s, t]_{max}.$$

Where $k_{max}$ is the index corresponding to the maximum, and $ARC[s,t]_{max}$ is total number of elements contributing to the meridian arc introduced by sample j of the transducer i.

4. The obtained sequences $\{I(k \leq k_{max})\}$ and $\{I(k \geq k_{max})\}$ are interpolated with separate 3-rd order polynomials as:

$$k = a_1 I(k)^3 + a_2 I(k)^2 + a_3 I(k) + a_4$$

5. The points of the polynomial bending are found as:

$$I(k_{bend}) = -\frac{a_2}{3a_1}, \text{ and}$$
$$k_{bend} = a_1 I(k_{bend})^3 + a_2 I(k_{bend})^2 + a_3 I(k_{bend}) + a_4$$

6. For $\{I(k \leq k_{max})\}$ all the pixels with $k > k_{bend}$ are used in MAAP image reconstruction. For $\{I(k \geq k_{max})\}$ all the pixels with $k < k_{bend}$ are used in MAAP image reconstruction.

7. Add the integrated signal $U_i(j)$ to the elements of matrix I' located at the same positions as the found pixels.

8. Repeat procedure 2-7 for each detector and each sample.

9. The final matrix I' represents the maximum angular amplitude probability reconstructed OA image.

EXAMPLE 2

Comparison of MAAP and RBP Reconstructed Images (Spherical Models)

Figure 2A:
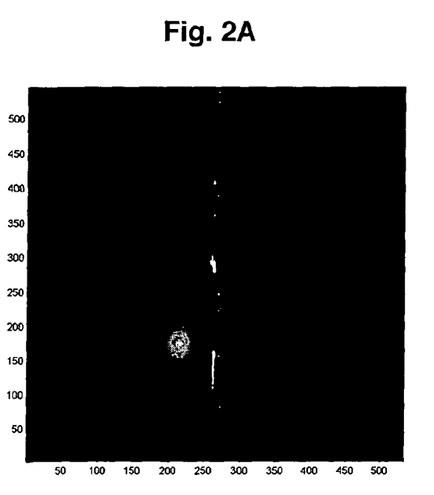
FIGS. 2A-2D are optoacoustic images of a 7 mm in diameter sphere provided by radial back projection (FIGS. 2A-2B) and maximum angular amplitude probability (FIGS. 2C-2D) image reconstruction algorithms. The pictures depicted in FIGS. 2A-2B are made using linear grayscale palette. The pictures depicted in FIGS. 2C-2D are made using triple-color threshold palette.
Figure 2B:
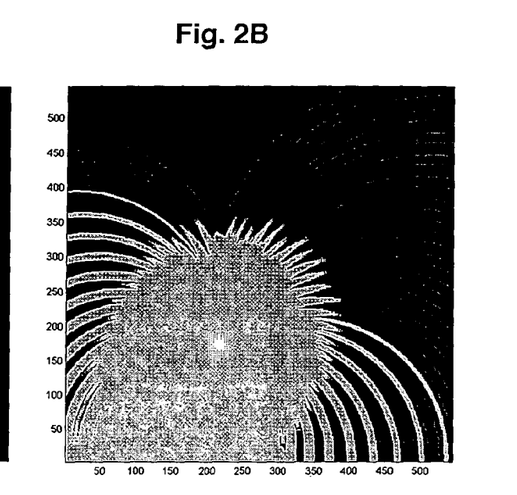
Figure 2C:
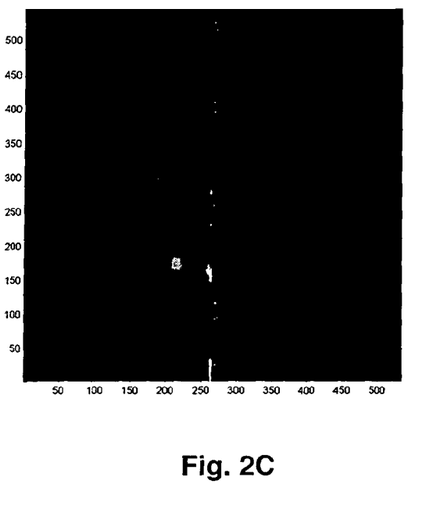
Figure 2D:
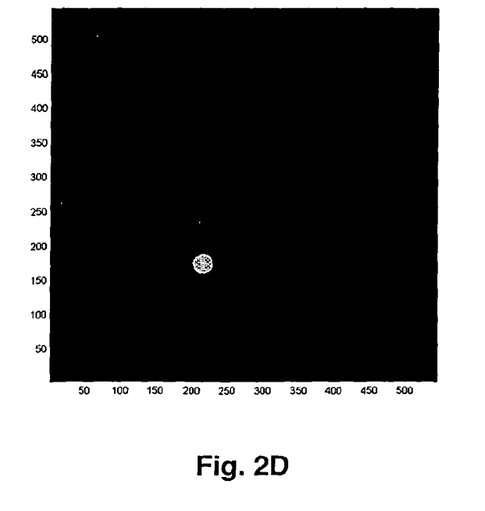
Figure 3A:
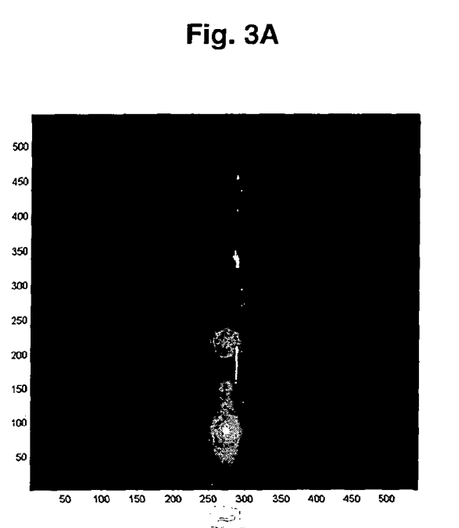
FIGS. 3A-3D are optoacoustic images of three equally absorptive spheres provided by radial back projection (FIGS. 3A-3B) and maximum angular amplitude probability (FIGS. 3C-3D) image reconstruction algorithms. The pictures depicted in FIGS. 3A-3B are made using linear grayscale palette. The pictures depicted in FIGS. 4C-4D are made using triple-color threshold palette.
Figure 3B:
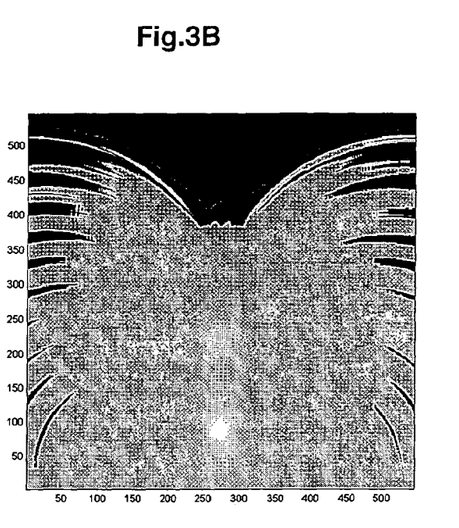
Figure 3C:
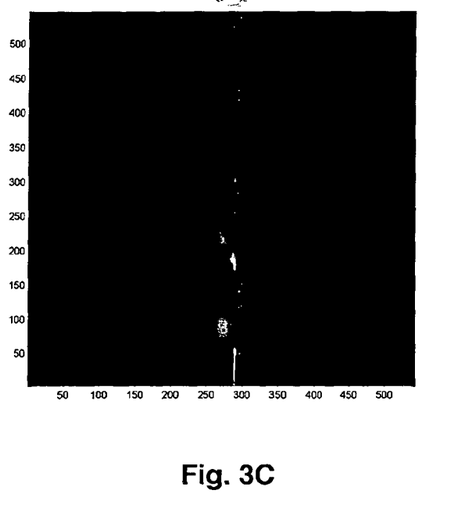
Figure 3D:
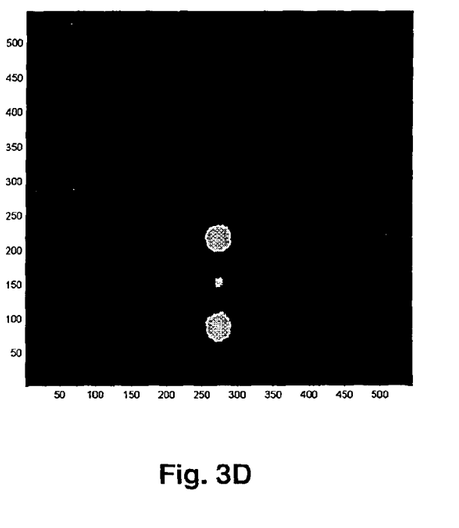
Figure 4A:
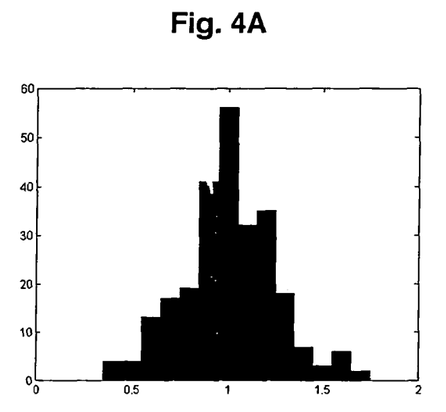
FIGS. 4A-4D show histograms obtained from quantitative OA tomography of spherical objects having K=1. Diameters ($D_{obj}$) and estimated median values $K_{med}$ are: $D_{obj}$=2 mm, $K_{med}$=1.01 (FIG. 4A); $D_{obj}$=5 mm, $K_{med}$=1.03 (FIG. 4B); $D_{obj}$=10 mm, $K_{med}$=1.00 (FIG. 4C); and $D_{obj}$=20 mm, $K_{med}$=1.00 (FIG. 4D).
Figure 4B:
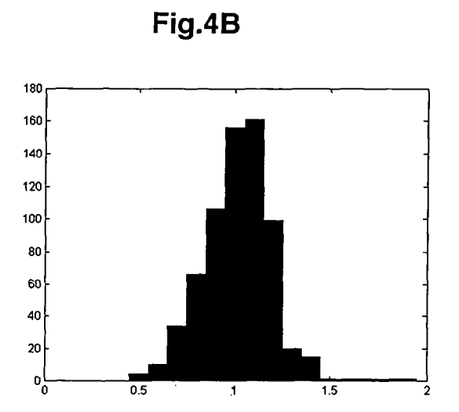
Figure 4C:
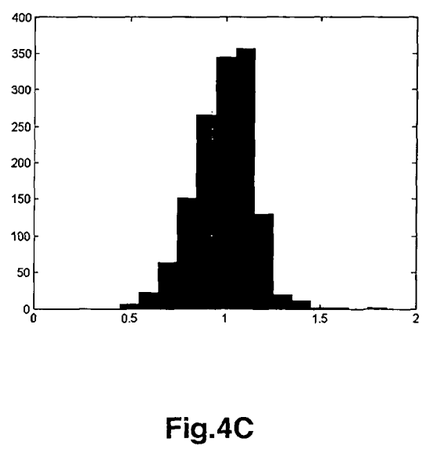
Figure 4D:
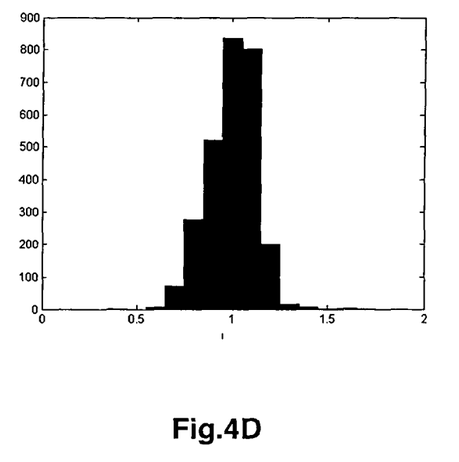

A radial back projection and maximum angular amplitude probability reconstructed optoacoustic images were compared using computer simulated signals from spherical absorptive objects. FIGS. 2A and 2B show a radial back projection image of a 7 mm in diameter absorptive object plotted using grayscale and triple-color threshold (hot metal palette shifted all the way to the cold colors) palettes. Image blurring as well as the artifacts in form of radiating arcs are clearly seen on FIGS. 2A-2B, respectively. Although linear grayscale maximum angular amplitude probability images (FIG. 2C) shrink and blur the object, triple-color threshold palette (FIG. 2D) reveals the true size of the object and recreates a high-contrast artifact-free image. Improvement of the optoacoustic image after maximum angular amplitude probability reconstruction is seen even more clearly when several objects of different size are simulated (FIGS. 3A-3D).

EXAMPLE 3

Examples of Quantitative OA Tomography Using Spherical Models

Figure 5A:
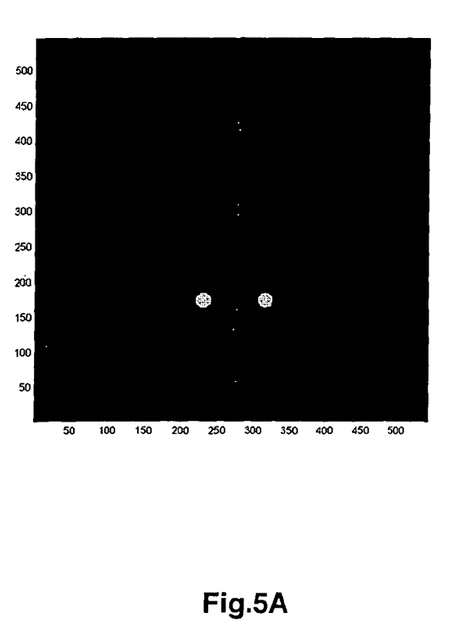
FIGS. 5A-5B are maximum angular amplitude probability images of two (FIG. 5A) and three (FIG. 5B) spherical objects with $D_{obj}$=5 mm and K=1. Estimated values of K are 0.98 and 0.93 (FIG. 5A) and 0.95, 0.93, and 0.94 (FIG. 5B).
Figure 5B:
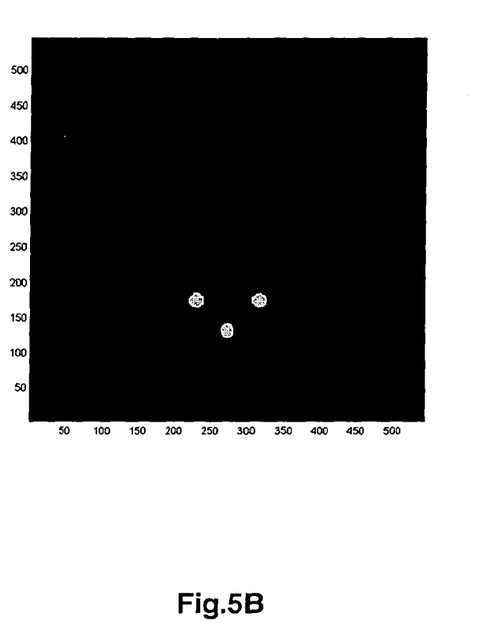

To demonstrate the accuracy of the offered approach for quantitative estimation of absorption coefficients, the algorithm is used that is described in Example 2 with signals obtained from spherical models, which had different diameters and the same unit absorption. FIGS. 4A-4D shows the histograms of the absorption coefficients found for single objects of 4 different diameters. The histograms show normally distributed K with a fairly small standard deviation. Considering the very large number of measurements, even for an object as small as 2 mm in diameter, the approach gives a very accurate estimation of the absorption coefficient where median values $K_{med}$, are close to the original value K=1. For several objects of interest the least squares solution to equation (18) still gives a very good estimate of absorption coefficients. FIGS. 5A-5B are examples of this for 2 and 3 objects.

One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

What is claimed is:

1. An optoacoustic imaging system for producing images of one or more objects in a body, configured to perform the steps of:

a) illuminating a body using pulses of electromagnetic radiation thereby generating a distribution of absorbed thermal energy under conditions of temporal pressure confinement within a volume of a resolution of interest;

b) detecting temporally resolved profiles of optoacoustic pressure signals generated within the volume of interest using one or more ultrasonic transducers;

c) processing the detected optoacoustic pressure signals to determine a value of absorbed electromagnetic energy;

d) determining a probability for each sample of the processed optoacoustic pressure signals to be received from a direction relative to each transducer using a radial backprojection algorithm; and e) applying a maximum angular amplitude probability (MAAP) algorithm effective to use directional information of the received optoacoustic signals relative to the transducer receiving the signal thereby reconstructing the high-contrast optoacoustic images of the body showing location, shape and true brightness of one or more objects within the body, thereby producing high-contrast optoacoustic images of the volume of interest; and f) fitting each reconstructed arc with a polynomial function and calculating the second derivative to determine exact boundaries of one or more objects for quantitative analysis of the reconstructed high-contrast optoacoustic images.

2. The optoacoustic imaging system of claim 1, wherein the illuminating step comprises:

delivering pulses of electromagnetic radiation to the body thereby producing a homogeneous distribution of an energy fluence within any given plane or slice inside the body that is perpendicular to the direction of the incident beam of the electromagnetic radiation.

3. The optoacoustic imaging system of claim 1, wherein the detecting step comprises:
   a) receiving the optoacoustic signals through an array of ultrawide-band ultrasonic transducers; or
   b) receiving the optoacoustic signals with a single ultrawide-band ultrasonic transducer scanned along the body.

4. The optoacoustic imaging system of claim 1, wherein the processing step comprises:
   a) amplifying and digitally recording the temporally resolved signals using an electronic data acquisition system;
   b) filtering all digitally recorded signals from noise while keeping the profiles of the optoacoustic signals unaltered;
   c) calculating either an integral of the temporally resolved optoacoustic signals or their time-derivative or a combination thereof resulting in enhanced contrast and optimal signal processing for quantitative analysis; and
   d) determining signal amplitude generated by objects only on those ultrasonic transducers that could separate all objects of diagnostic interest by detecting them at different time positions.

5. The optoacoustic imaging system of claim 4, wherein the transducers have a transducer directivity of about 0 to about $2\pi$ steradians and with an angular aperture of the array of about 0 and $4\pi$ steradians.

6. An optoacoustic imaging system for producing maps of one or more objects in a body, configured to perform the steps of:
   a) illuminating the body with pulses of electromagnetic radiation thereby producing a homogeneous distribution of an energy fluence within any given plane inside the body perpendicular to the direction of the incident beam of the electromagnetic radiation;
   b) detecting temporally resolved profiles of resulting optoacoustic signals using an array of ultrawide-band ultrasonic transducers with transducer directivity of about 0 to about $2\pi$ steradians and with an angular aperture of the army of about 0 and $4\pi$ steradians;
   c) amplifying and digitally recording the temporally resolved signals using an electronic data acquisition system;
   d) filtering all digitally recorded signals from noise while keeping the profiles of the optoacoustic signals unaltered;
   e) optimally processing the temporally resolved signals to convert bipolar pressure signals into monopolar signals
   f) reconstructing optoacoustic images of the body using a radial backprojection algorithm effective to determine a probability for each sample of an optoacoustic signal to be received from a direction relative to the transducer;
   g) applying a maximum angular amplitude probability algorithm effective to use information on the direction of the received optoacoustic signals relative to the transducer thereby reconstructing high-contrast optoacoustic images of the body showing location and shape of the one or more objects;
   h) fitting each reconstructed arc with a polynomial function and calculating the second derivative to determine exact boundaries of one or more objects;
   i) assigning each of the determined objects inside the body with an unknown absorption coefficient;
   j) using each sample of the integral of the temporally resolved optoacoustic profiles received by each transducer to solve a linear regression model of unknown absorbtion coefficients with regression coefficients related to determined sizes of the objects; and
   k) plotting the optoacoustic map based on determined absorption coefficients of the one or more objects inside the body.

7. The optoacoustic imaging system of claim 6, wherein the object is a single object and step i) comprises:
   a) using each sample of the integral of the temporally resolved optoacoustic profiles received by each transducer to calculate an average absorption coefficient of an arc in the object while accounting for individual size of the image pixel and the number of pixels in the arc within the object; and
   b) using statistical distribution of the average absorption coefficients of the arcs to estimate the true absorption coefficient of the object.

8. The optoacoustic imaging system of claim 6, wherein the directivity of each transducer is about zero, and step l) comprises:
   reconstructing the optoacoustic images of the body by placing measured sample values of the integrated optoacoustic signals to the pixels of the map along the line of directivity of each acoustic transducer.

9. The optoacoustic imaging system of claim 6, wherein the map of the one or more objects comprises a tool for diagnosis of a pathophysiological condition of the body characterized by abnormal optical properties of tissues or to establish the location and absolute value of the same.

10. The optoacoustic imaging system of claim 9, wherein the pathophysiological condition is a breast cancer, a prostate cancer, skin cancer, a vascular skin disorder, a brain hemorrhage, a hematoma, a heart disease, atherosclerotic plaques, arthritis, an ocular disease, any tissue deprived from blood supply due to the pathophysiological condition or other condition with abnormal optical properties of tissues.

11. An optoacoustic imaging system for diagnosing a pathophysiological condition characterized by abnormal optical properties of tissues in a body, configured to perform the steps of:
   a) obtaining temporally resolved profiles of acoustic signals generated by one or more objects associated with the pathophysiological condition within a body upon illumination thereof with electromagnetic radiation;
   b) applying at least a maximum angular amplitude probability algorithm to the profiles to determine optical absorption coefficients of the one or more objects to reconstruct high-contrast optoacoustic images of the body; and
   c) plotting an optoacoustic map based on the determined optical absorption coefficients of one or more objects showing a location thereof inside the body thereby diagnosing the pathophysiological condition.

12. The optoacoustic imaging system of claim 11, wherein the electromagnetic radiation is pulsed thereby producing a homogeneous distribution of an energy fluence within any given plane or slice inside the body that is perpendicular to the direction of the incident beam of the electromagnetic radiation.

13. The optoacoustic imaging system of claim 11, wherein the obtaining step comprises;
   a) receiving the acoustic signals through an array of ultrawide-band ultrasonic transducers;
   b) amplifying and digitally recording the temporally resolved signals using an electronic data acquisition system; and
   c) filtering all digitally recorded signals from noise while keeping the profiles of the acoustic signals unaltered.

14. The optoacoustic imaging system of claim 13, wherein the transducers have a transducer directivity of about 0 to about $2\pi$ steradians and with an angular aperture of the array of about 0 and $4\pi$ steradians 15. The optoacoustic imaging system of claim 11, wherein the applying step comprises:
    a) determining a probability for each sample of the acoustic signal to be received from a direction relative to the transducer using a radial backprojection algorithm;
    b) applying a maximum angular amplitude probability algorithm effective to use information on the direction of the received acoustic signals relative to the transducer receiving the signal thereby reconstructing the high-contrast optoacoustic images of the body showing location and shape of one or more objects;
    c) fitting each reconstructed arc with a polynomial function and calculating the second derivative to determine exact boundaries of one or more objects;
    d) assigning each of the determined objects inside the body with an unknown absorption coefficient; and
    e) using each sample of the integral of the temporally resolved optoacoustic profiles received by each transducer to solve a linear regression model of unknown absorption coefficients with regression coefficients related to determined sizes of the objects.

16. The optoacoustic imaging system of claim 15, wherein the object is a single object and step e) comprises:
    a) using each sample of the integral of the temporally resolved optoacoustic profiles received by each transducer to calculate an average absorption coefficient of an arc in the object while accounting for individual size of the image pixel and the number of pixels in the arc within the object; and
    b) using statistical distribution of the average absorption coefficients of the arcs to estimate the true absorption coefficient of the object.

17. The optoacoustic imaging system of claim 15, wherein directivity of each transducer is about zero and step e) comprises:
    placing measured sample values of the integrated optoacoustic signals to the pixels of the map along the line of directivity of each acoustic transducer.

18. The optoacoustic imaging system of claim 11, further comprising:
    administering an optoacoustic contrast agent effective to alter optical absorption of specific objects or locations of diagnostic interest in the body.

19. The optoacoustic imaging system of claim 11, wherein the pathophysiological condition is a breast cancer, a prostate cancer, skin cancer, a vascular skin disorder, a brain hemorrhage, a hematoma, a heart disease, atherosclerotic plaques, arthritis, an ocular disease, any tissue deprived from blood supply due to the pathophysiological condition or other condition with abnormal optical properties of tissues.

* * * * *